United States Patent
Fu et al.

(10) Patent No.: US 9,297,772 B2
(45) Date of Patent: Mar. 29, 2016

(54) APPARATUS FOR AMPLIFYING INTENSITY DURING TRANSMISSION SMALL ANGLE—X-RAY SCATTERING MEASUREMENTS

(71) Applicant: Industrial Technology Research Institute, Hsinchu (TW)

(72) Inventors: Wei-En Fu, Hsinchu (TW); Wen-Li Wu, Hsinchu (TW)

(73) Assignee: Industrial Technology Research Institute, Chutung Township, Hsinchu County (TW)

( * ) Notice: Subject to any disclaimer, the term of this patent is extended or adjusted under 35 U.S.C. 154(b) by 48 days.

(21) Appl. No.: 14/246,702

(22) Filed: Apr. 7, 2014

(65) Prior Publication Data
US 2015/0036805 A1 Feb. 5, 2015

Related U.S. Application Data

(60) Provisional application No. 61/891,062, filed on Oct. 15, 2013, provisional application No. 61/859,838, filed on Jul. 30, 2013.

(51) Int. Cl.
*G21K 1/00* (2006.01)
*G01N 23/201* (2006.01)

(52) U.S. Cl.
CPC .................... *G01N 23/201* (2013.01)

(58) Field of Classification Search
CPC .............................. G21K 1/06; G01N 23/201
USPC ..................... 378/70–90, 145–155
See application file for complete search history.

(56) References Cited

U.S. PATENT DOCUMENTS

| | | | |
|---|---|---|---|
| 7,889,838 B2 | 2/2011 | David et al. | |
| 2009/0316857 A1* | 12/2009 | David .................... | A61B 6/484 378/62 |
| 2012/0145912 A1* | 6/2012 | Iwakiri et al. ............ | 250/370.08 |
| 2013/0094625 A1 | 4/2013 | Huang et al. | |

FOREIGN PATENT DOCUMENTS

| | | |
|---|---|---|
| CN | 10157615 | 11/2009 |
| CN | 102428522 | 4/2012 |
| CN | 102740775 A | 10/2012 |
| CN | 101532969 B | 4/2013 |

(Continued)

OTHER PUBLICATIONS

Hu et al., "Small angle x-ray scattering metrology for sidewall angle and cross section of nanometer scale line gratings", Journal of Applied Physis, 2004, pp. 1983-1987, vol. 96.

(Continued)

*Primary Examiner* — Courtney Thomas
(74) *Attorney, Agent, or Firm* — Muncy, Geissler, Olds & Lowe, P.C.

(57) ABSTRACT

The disclosure provides an apparatus for amplifying scattering intensity during tSAXS measurements. The apparatus includes an enhancement grating object and a placement mechanism. The enhancement grating object is positioned within a longitudinal coherence length of an incident X-ray from a target object. The placement mechanism is capable of placing the enhancement grating object with nanometer precision with respect to the target object in both a lateral and a longitudinal directions.

12 Claims, 9 Drawing Sheets

(56) References Cited

FOREIGN PATENT DOCUMENTS

| | | |
|---|---|---|
| CN | 103068310 | 4/2013 |
| EP | 2531105 | 12/2012 |
| JP | 09-269303 | 10/1997 |
| JP | 2009-543080 | 12/2009 |
| JP | 2012-85995 A | 5/2012 |
| TW | 201213791 A | 4/2012 |
| WO | WO98/33062 A1 | 7/1998 |
| WO | WO 2011/096584 A1 | 8/2011 |
| WO | WO2011096584 | 8/2011 |
| WO | WO2013004574 | 1/2013 |

OTHER PUBLICATIONS

Jones et al., "Small angle x-ray scattering for sub-100 nm pattern characterization", Applied Physis Letters, 2003, pp. 4059-4061, vol. 83, No. 19.

Wu et al., "Small angle neutron scattering measurements of nanoscale lithographic features", Journal of Applied Physics, 2000, pp. 7298-7303, vol. 88, No. 12.

Jones et al., "Sub-nanometer wavelength metrology of lithographically prepared structures: A comparison of neutron and X-ray scattering", Proceedings of SPIE, 2003, pp. 191-199, vol. 5038.

Wang et al., "Small angle x-ray scattering measurements of lithographic patterns with sidewall roughness from vertical standing waves", Applied Physics Letters, 2007, pp. 193122-1-193122-3, vol. 90.

Wang et al., "CD-SAXS measurements using laboratory-based and synchrotron-based instruments", Proc. of SPIE, 2008, pp. 69222e-1-69222e-7, vol. 6922.

Wang et al., "Small angle X-ray scattering measurements of spatial dependent linewidth in dense nanoline gratings", Thin Solid Films, 2009, pp. 5844-5847, vol. 517.

\* cited by examiner

APPARATUS FOR AMPLIFYING INTENSITY DURING TRANSMISSION SMALL ANGLE—X-RAY SCATTERING MEASUREMENTS

CROSS-REFERENCE TO RELATED APPLICATION

All related applications are incorporated by reference.

The application is based on, and claims priority from, U.S. Provisional Application Ser. No. 61/859,838, filed on Jul. 30, 2013 and U.S. Provisional Application Ser. No. 61/891,062, filed on Oct. 15, 2013, the disclosure of which is hereby incorporated by reference herein in its entirety.

TECHNICAL FIELD

The technical field relates to an apparatus for amplifying intensity during transmission small angle X-ray scattering measurements.

BACKGROUND

Transmission SAXS (tSAXS) has been identified as a potential solution for measuring nanoscale features by interrogating structures with sub-nanometer wavelength X-ray radiation. Most relevant parameters describing critical dimensions (CDs) of nanoscale features are pitch, pitch variations, side wall angle, line edge roughness, line width roughness and so forth. Based on the spacing of diffraction peaks, the parameter (pitch) can be extracted from the tSAXS scattering pattern. The geometric form factors of a structure can be extracted from the envelope function of the scattering intensity. In addition to the CDs of a structure, tSAXS has been used to successfully characterize LER, pitch walk, nonplanar film thicknesses on sidewalls and complicated profiles of a memory structure that requires a 6-trapezoid model. Since the X-ray wavelength is still much smaller than the feature size of today's nanoscale structure, the tSAXS technique will stay as a viable CD metrology in the future. Actually the applicability of tSAXS will improve at future technology nodes where more densely packed features or an ever decreasing pitch will result in widely apart scattering peaks; thus, more readily detectable via tSAXS. Additionally, it avoids the issues related to optical properties, e.g. n and k, their wavelength and size dependences since tSAXS is based on classical X-ray elastic scattering, the observed scattering intensity depends only on variation in local electron density.

SUMMARY

The disclosure provides an apparatus for amplifying scattering intensity during tSAXS measurements. The apparatus includes an enhancement grating object and a placement mechanism. The enhancement grating object is positioned within a longitudinal coherence length of an incident X-ray from a target object. The placement mechanism is capable of placing the enhancement grating object with nanometer precision with respect to the target object in both a lateral and a longitudinal directions.

BRIEF DESCRIPTION OF DRAWINGS

The disclosure can be more fully understood by reading the following detailed description of the preferred embodiments/examples, with references made to the accompanying drawings, wherein.

the above conditions lead to $\cos(q_x\eta)=0$ according to the disclosure.

Figure 5A:
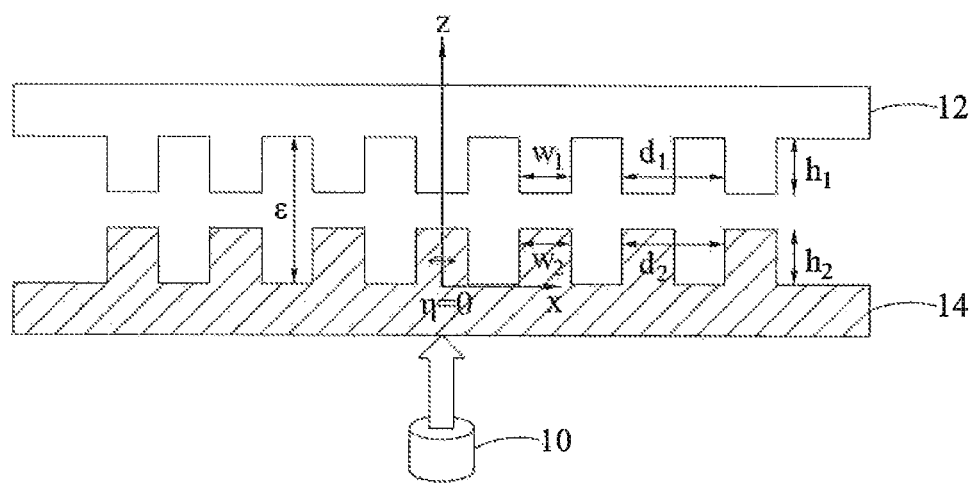
FIG. 5a is a schematic diagram illustrating identical materials for both the target object and the enhancement grating object with $f=1$, $\alpha=1$, $m_1=m_2=2$ and $\eta=0$, the above conditions lead to $\cos(q_x\eta)=1$ according to the disclosure.
Figure 5B:
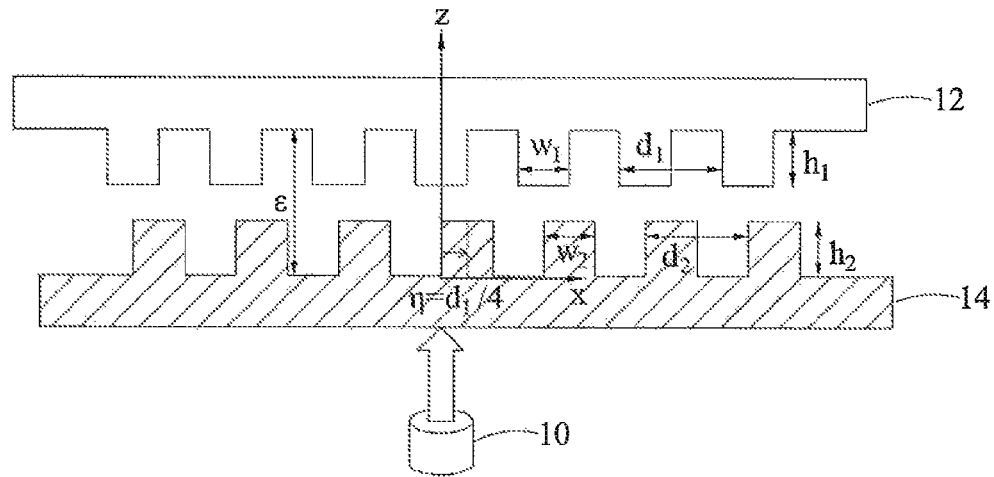
FIG. 5b is a schematic diagram illustrating identical materials for both the target object and the enhancement grating object with $f=1$, $\alpha=1$, $m_1=m_2=2$ and $$\eta = \frac{d_1}{4},$$
Figure 5C:
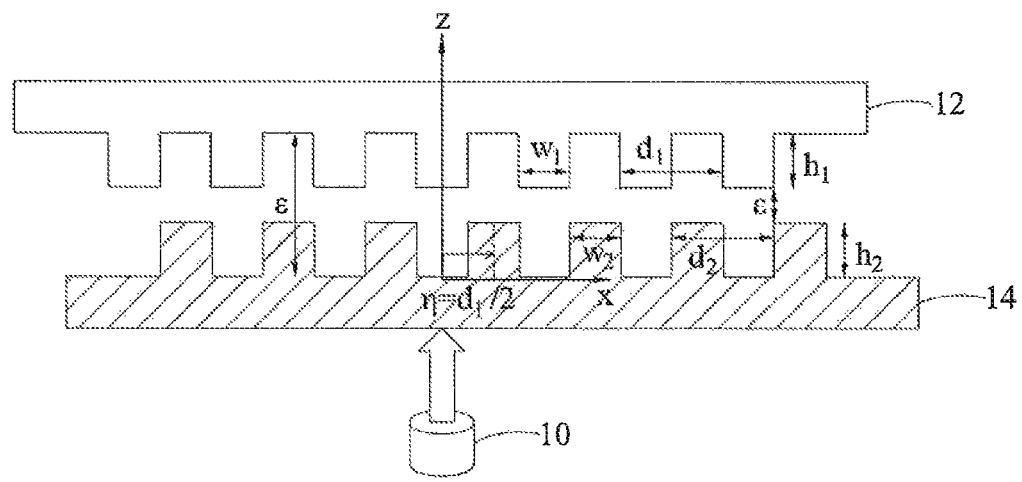

FIG. 5c is a schematic diagram illustrating identical materials for both the target object and the enhancement grating object with $f=1$, $\alpha=1$, $m_1=m_2=2$ and $$\eta = \frac{d_1}{2},$$

the above conditions lead to $\cos(q_x\eta)=1$ according to the disclosure.

Figure 6:
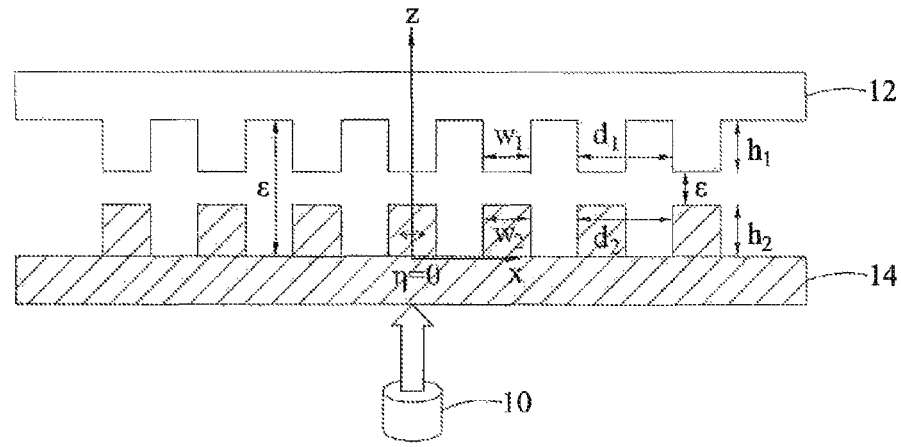

FIG. 6 is a schematic diagram illustrating the enhancement grating object made of Cu and the target object made of Si in perfect alignment when $\eta=0$ according to the disclosure.

Figure 7:
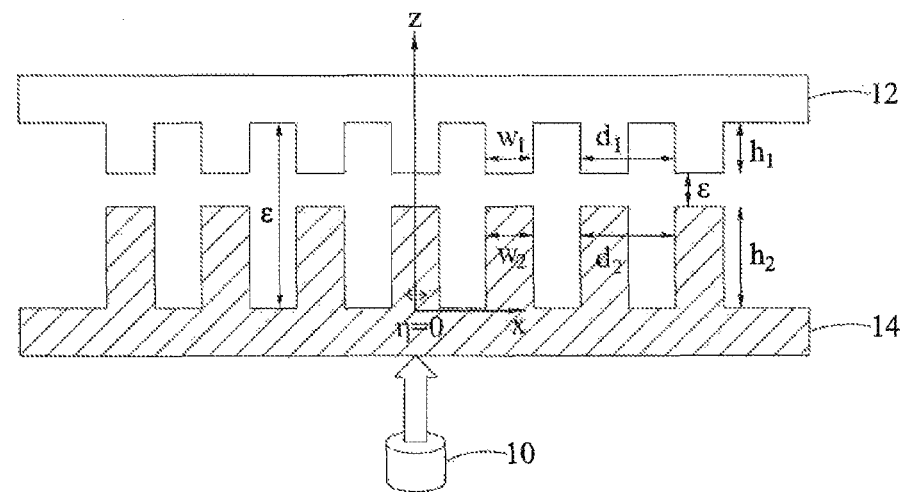

FIG. 7 is a schematic diagram illustrating identical materials for both the target object and the enhancement grating object when $h_2=10h_1$ for $f=10$ in perfect alignment ($\eta=0$) according to the disclosure.

Figure 8:
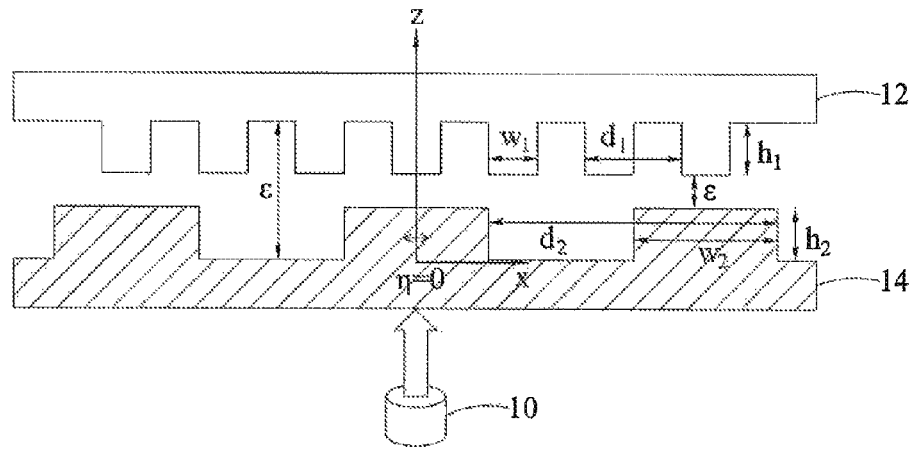

FIG. 8 is a schematic diagram illustrating identical materials for both the target object and the enhancement grating object when $d_2=3d_1$ in perfect alignment ($\eta=0$) according to the disclosure.

Figure 9:
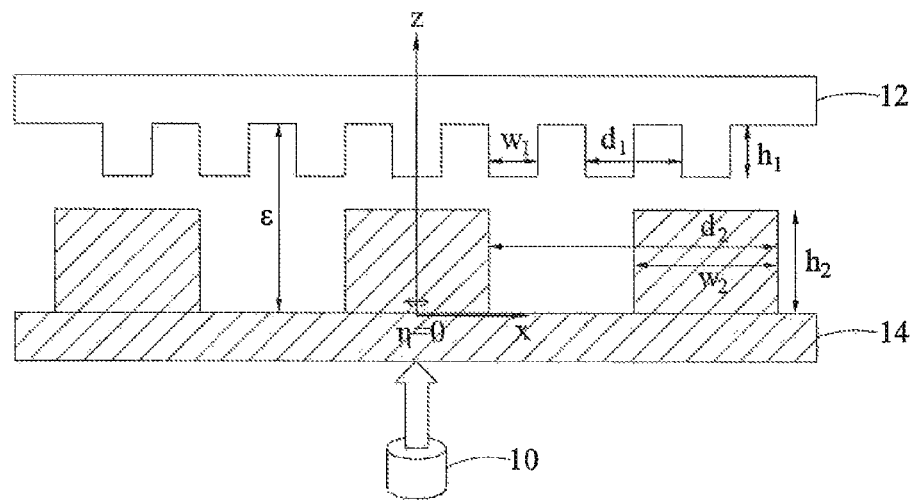

FIG. 9 is a schematic diagram illustrating the enhancement grating object made of Cu and the target object made of Si with $m_1=m_2=2$ when $h_2=10h_1$ and $d_2=3d_1$ according to the disclosure.

Figure 10:
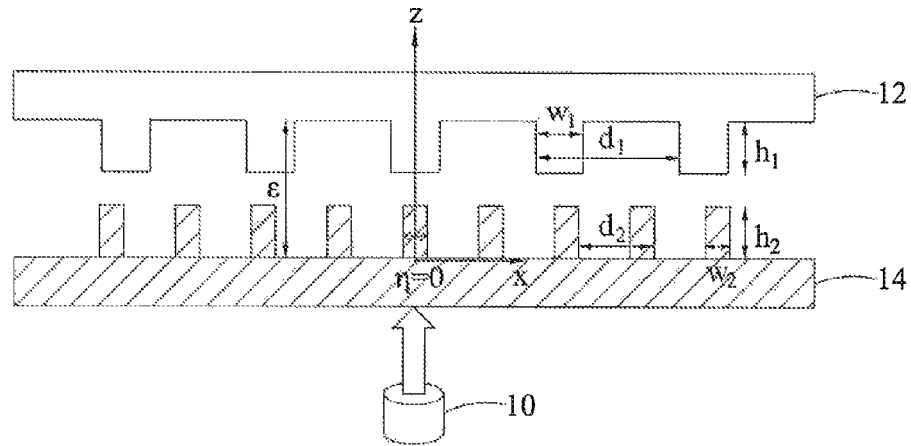

FIG. 10 is a schematic diagram illustrating the enhancement grating object made of Cu and the target object made of Si when $h_2=h_1$ and $$d_2 = \frac{1}{2}d_1$$

as well as the line width is one third of the pitches for both objects according to the disclosure.

Figure 11:
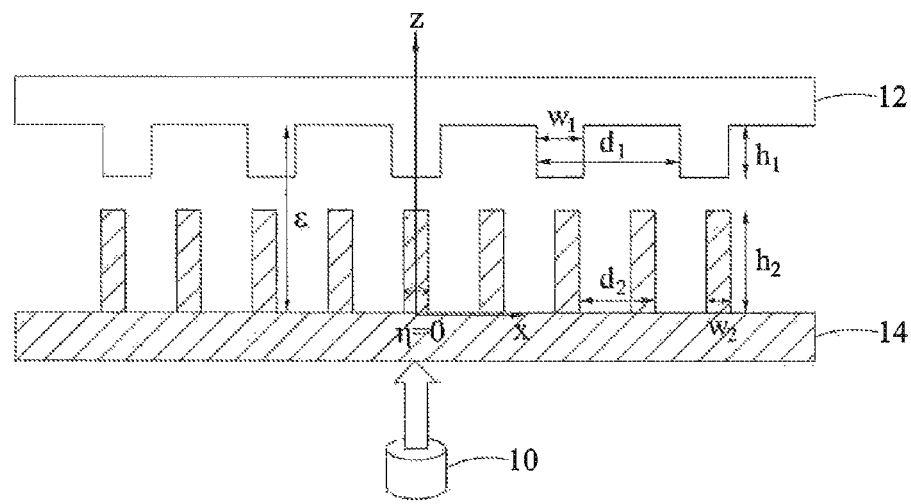

FIG. 11 is a schematic diagram illustrating the enhancement grating object made of Cu and the target object made of Si when $h_1=5h_2$ and $$d_2 = \frac{1}{2}d_1$$

as well as the line width is one third of the pitches for both objects according to the disclosure.

DETAILED DESCRIPTION

The following embodiments are described in sufficient detail to enable those skilled in the art to make and use the disclosure. It is to be understood that other embodiments would be evident based on the disclosure, and that system or mechanical changes may be made without departing from the scope of the disclosure.

In the following description, numerous specific details are given to provide a thorough understanding of the disclosure. However, it will be apparent that the disclosure may be practiced without these specific details. In order to avoid obscuring the disclosure, some well-known mechanisms and system configurations are not disclosed in detail.

The drawings showing embodiments of the architecture are semi-diagrammatic and not to scale and, particularly, some of the dimensions are for clarity of presentation and are shown exaggerated in the drawings. Similarly, although the views in the drawings for ease of description generally show similar orientations, this depiction in the drawings is arbitrary for the most part. Generally, the disclosure can be operated in any orientation.

The disclosure is described by the following specific embodiments and examples. Those with ordinary skills in the arts can readily understand the other functions of the disclosure after reading the disclosure of this specification. The disclosure can also be implemented with different embodiments and examples. Various details described in this specification can be modified based on different viewpoints and applications without departing from the scope of the disclosure.

Figure 1:
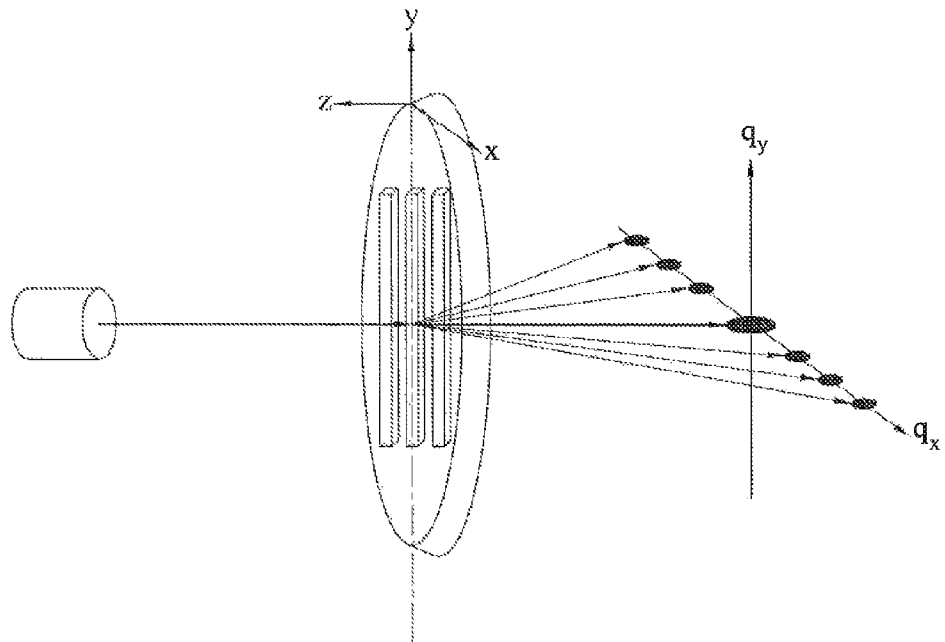
FIG. 1 is a schematic diagram depicting a transmission small-angel X-ray scattering (tSAXS) system. The collimation part of the system located between the X-ray source and the sample is not shown.

FIG. 1 shows a schematic diagram of a transmission small-angel X-ray scattering (tSAXS) technique.

tSAXS has mostly been performed using the synchrotron X-ray source for its high beam flux or high brilliance. The scattering cross section of nanoscale features is intrinsically small due to their small scattering volume. With a feature size of 20 nm, for example, its height is typical 30~50 nm or about 2 times that of the feature size, its scattering volume is just the beam cross section times 30~50 nm, a minuscule value. Synchrotron X-ray sources have sufficient brilliance to overcome the abovementioned difficulty, however, they are simply too large and too expensive for daily industrial deployment. A lab system with a Molybdenum rotating anode X-ray source has been successfully demonstrated for this type of applications in National Institute of Standards and Technology (NIST), but the measurement speed is too slow for high volume manufacturing (HVM). A recent development in X-ray source results in a liquid-metal jet source which can provide a significant increase in brilliance, and this is expected to result in an increase in measurement speed. However, such increase in measurement speed is still not enough to enable tSAXS for HVM applications. The disclosure is to provide an apparatus for enhancing X-ray scattering intensity from a target object (the structures of interests). The enhancement of X-ray scattering intensity can lead to an increase in measurement speed as well as an improvement in signal quality.

An X-ray beam irradiates on the gratings (structures) on Si wafer (or substrate) and a significant portion of the incident beam passes through the substrate with the scattered or diffracted beam moving toward the detector. Since wavelengths of the incident X-rays are much smaller than gratings (or structures), the X-rays can resolve the features of the gratings (structures) in many current and future IC generations. In light of the alignment of measurements in the tSAXS, the X-rays can either incident on gratings first, and the scattered X-rays pass through Si wafer (or substrate), or pass through Si wafer (or substrate) first, and scatter from the gratings (or structures). Either way, the scattered X-rays (or diffracted X-rays) are detected by a spatially resolved detector. The pitch and pitch variation of the gratings can be obtained from major diffraction peaks and intensity decay with increasing order. The other geometric form factors, such as SWA, LER, and LWR, are correlated with the envelope function of the diffraction intensities. However, due to the limitation of the X-ray intensity or flux provided by the laboratory X-ray source, the measurements for CDs require many hours. While this time frame makes the technique useful as a research and development tool, significant throughput improvement is required to make the tSAXS practical to meet the grand challenges for in-line IC metrology applications.

The X-ray source is a laboratory source, a synchrotron light source providing a high X-ray flux and many other X-ray sources.

In order to increase the throughput for high volume manufacturing (HVM), the detectable X-ray scattering intensity or intensity envelop function of diffraction patterns are also required to shorten the collection time. Accordingly, the disclosure provides an apparatus for amplifying scattering intensity from a target object 12 using an enhancement grating object 14 during tSAXS measurements.

Throughout this disclosure the words "scattering" and "diffraction" are used interchangeably; moreover, the phase of "amplify or enhance scattering intensity" does not necessarily imply that the scattering intensity at certain angles from a target object is increased literally. As to be demonstrated in the forthcoming embodiments of the disclosure, the enhancement of the scattering intensity or signal from a target object often manifests itself by a significantly decrease or increase in the scattering intensity from the background scattering intensities arisen from an enhancement object. In essence, it is the scattering signals or contributions from the target object becoming more discernable by applying the technique described in this disclosure; the contribution of scattering intensity from the target object can either be positive or negative.

Figure 2:
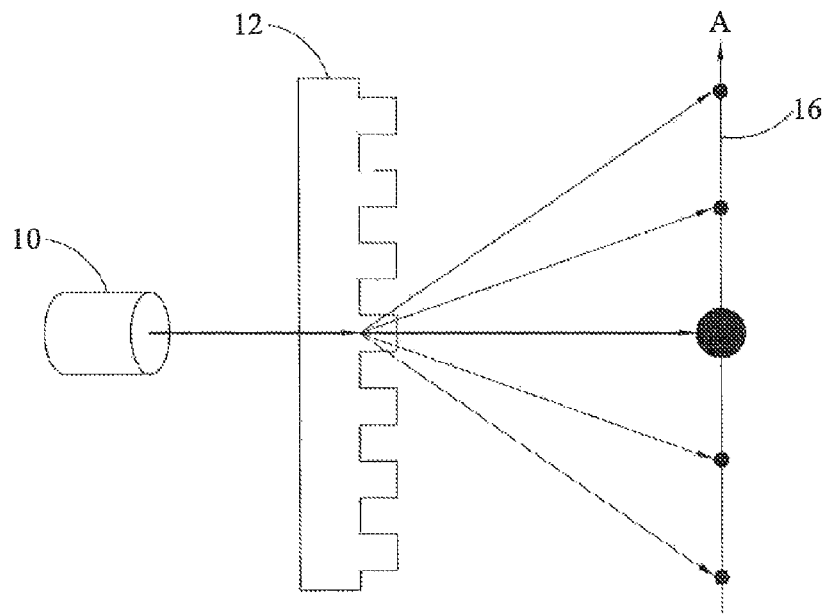
FIG. 2 is a schematic diagram depicting the tSAXS measurement for a target object (one-dimensional (1-D) grating) according to one exemplary embodiment of the disclosure.

FIG. 2 shows that the tSAXS is applied for measuring a patterned target object (shown in one-dimension). The X-ray scattered pattern can be measured by the spatially resolved detector 16, as shown in FIG. 2.

According to the disclosure, the scattering intensity from the target object 12 (grating) can be described as:

$$I \propto \Delta b_1^2 \times F_1^2(q) \qquad (1)$$

where $\Delta b_1^2$ is a contrast factor of the target object 12 and its value is rather small in most nanoscale patterns. $F_1(q)$ is the Fourier transform of the target object and q is defined in its typical way as $(4\pi/\lambda) \sin \theta$, where $\lambda$ denotes the X-ray wavelength and $\theta$ is the scattering angle. Throughout this disclosure both the target and the enhancement objects are symmetric about their origin, hence all $F(q)$ are real in value, i.e. with no imaginary component.

Figure 3A:
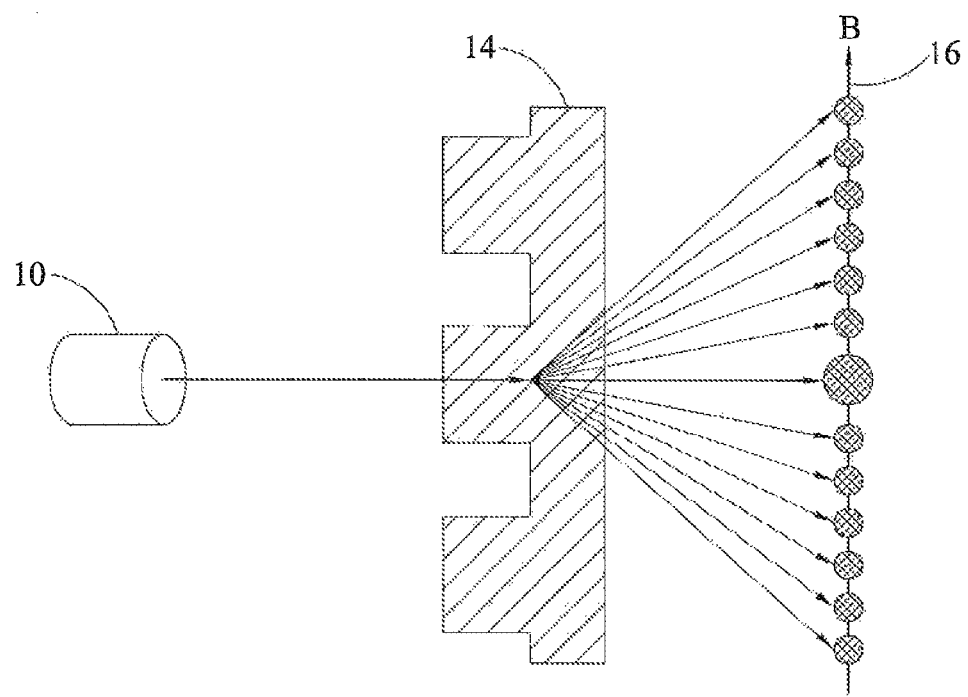
FIG. 3a is a schematic diagram illustrating the tSAXS measurement for an enhancement grating object (1-D grating) according to one exemplary embodiment of the disclosure.
Figure 3B:
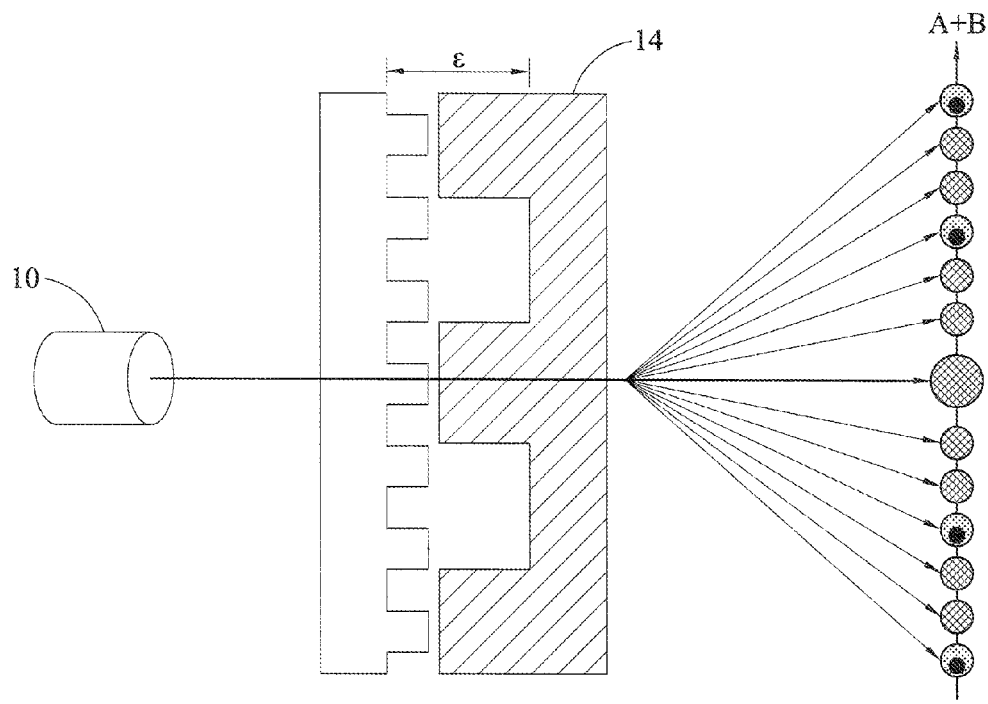
FIG. 3b is a schematic diagram illustrating the tSAXS measurement for the increase of the X-ray scattering intensity at the third and the sixth peaks from the target object according to one exemplary embodiment of the disclosure.
Figure 3C:
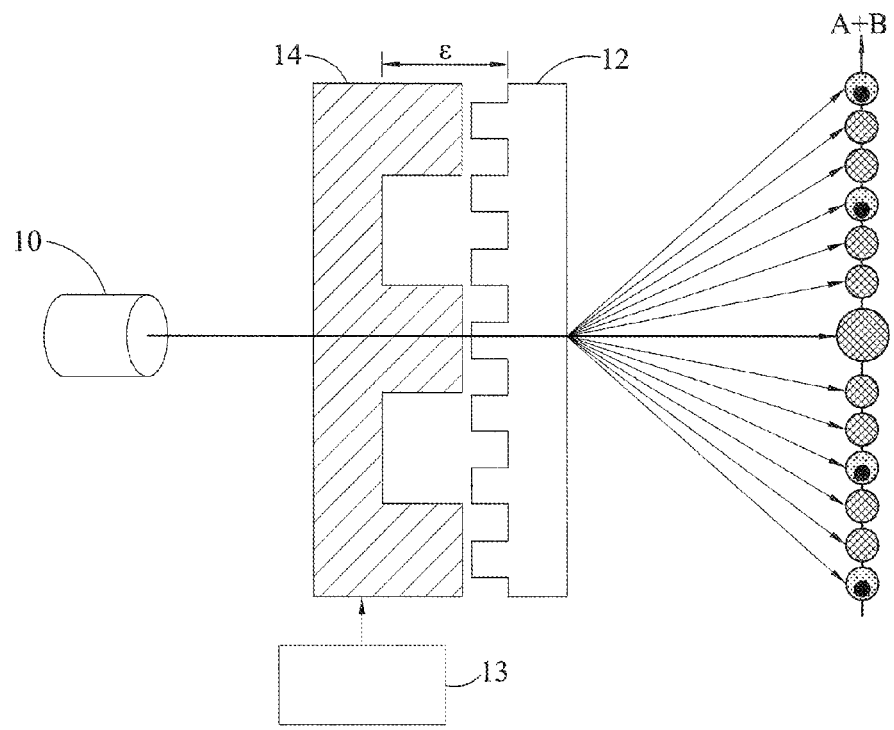
FIG. 3c is a schematic diagram illustrating the tSAXS measurement for the increase of the X-ray scattering intensity at the third and the sixth peaks from the target object according to anther embodiment of the disclosure.

An additional pattern (i.e., the enhancement grating object 14) with strong scattering cross section, as shown in FIG. 3a, is added into the path of the transmitted SAXS in between the target object 12 and the detector 16, as shown in FIG. 3b. As shown in FIG. 3b, the solid dots represent the positions of the peak intensities that refracted by the target object 12, and the grid shadings represent the positions of the peak intensities that refracted by the enhancement grating object 14. The screen tones, i.e. the overlapping portion of the solid dots and the grid shadings, represent the positions of the peak intensities that refracted by the target object 12 and the enhancement grating object 14. In practice or in the application of semiconductor industry in-line measurements, the enhancement grating object 14 will be positioned in between the X-ray source and the target object 12, as shown in FIG. 3c. Both configurations provide the same enhancement for the X-ray intensity received by the X-ray detector 16.

An apparatus for amplifying scattering intensity during tSAXS measurements, includes: an enhancement grating object 14 positioned within a longitudinal coherence length of an incident X-ray from a target object 12; and a placement mechanism 13 capable of placing the enhancement grating object 14 with nanometer precision with respect to the target object 12 in both a lateral and a longitudinal direction.

The enhancement grating object is positioned either at a back of the target object or at a front of the target object, as shown in FIGS. 3b and 3c.

The enhancement grating object 14 is configured to be shifted laterally or longitudinally with respect to the target object with nanometer precision during tSAXS measurements.

The enhancement grating object 14 is used as a reference object to facilitate critical dimension (CD) characterization of the target object with a single or multiple layered structure.

The enhancement grating object 14 is a one-dimensional (1-D) grating object, a two-dimensional (2-D) grating object, arrays of holes, pillars and other periodical structures.

Upon the weak scattering object (i.e., the target object 12), the strong scattering object (i.e., the enhancement grating object) is positioned within the longitudinal coherence length $\epsilon$ of the X-rays of the weak scattering object, as shown in FIG. 3b-c. The observed scattering intensity becomes $$I(q) \propto |\Delta b_1 \times F_1(q) + \Delta b_2 \times F_2(q)|^2 \quad (2)$$

where the second grating object denotes the enhancement grating object 14 with a strong scattering for intensity enhancement.

Eq. (2) can be expended as follows:

$$\Delta b_1^2 \times F_1^2(q) + \Delta b_2^2 \times F_2^2(q) + 2\Delta b_1 \Delta b_2 |F_1(q) F_2(q)| \quad (3)$$

where $2\Delta b_1 \Delta b_2 |F_1(q) F_2(q)|$ is the interaction term of the enhancement grating object 14 and the target object 12. The interaction term $2\Delta b_1 \Delta b_2 |F_1(q) F_2(q)|$ carries information of the target object 12, and its magnitude can be significantly greater than $\Delta b_1^2 \times F_1^2(q)$ alone, since the value of $\Delta b_2^2$ and $F_2^2(q)$ can be much greater than those of the target object 12.

Regarding the enhancement grating object 14 positioned within the longitudinal coherence length $\epsilon$ with the target object 12, the enhancement to different extent in the X-ray scattering intensity can be achieved by varying the physical dimensions and materials of the enhancement grating object 14. For semiconductor manufacture applications, the preferred wavelengths of the X-rays are around 0.1 nm or smaller.

In the following embodiments, both the target object 12 and the enhancement grating object 14 are line gratings with rectangular cross section lines. As shown in FIG. 2 and FIG. 3a, all the diffraction spots are appeared along $q_x$ with $q_y=0$. The function $F_i(q)$ can be replaced by $F_i(q_x)$, and can be explicitly expressed as:

$$F_i(q_x) = w_i \frac{\sin\left(\frac{w_i q_x}{2}\right)}{\frac{w_i q_x}{2}} \times \frac{2\pi}{d_i} \sum_{n_i=-\infty}^{+\infty} \delta\left(q_x - n_i \frac{2\pi}{d_i}\right) \quad (4)$$

$$= \sum_{n_i=-\infty}^{+\infty} \frac{2}{n_i} \sin\left(n_i \pi \frac{w_i}{d_i}\right) \delta\left(q_x - n_i \frac{2\pi}{d_i}\right)$$

where $\delta$ denotes the Dirac delta, w denotes the width of an individual line, d is the pitch of grating and $n_i$ is the order of the scattering peak. In Eq. (4) the height h of the line does not appear explicitly since its value is included in the contrast factor $\Delta b$ as $\Delta b \propto h \times \rho$, where $\rho$ is the electron density of the grating material, and is defined as the total number of electrons within unit volume. For silicon, copper and polystyrene, their values of $\rho$ are $6.80 \times 10^{23}/cm^3$, $24.44 \times 10^{23}/cm^3$ and $3.44 \times 10^{23}/cm^3$, respectively. Polystyrene is included to represent typical photoresists. The scattering intensity is proportional to the second power of $F_i(q_x)$, thus, its value will decrease as $n^{-2}$ as indicated by Eq. (4). Let's denote the ratio w/d as 1/m, Eq. (4) indicates that the peak intensity at n=m, 2m, 3m, . . . all vanishes. For example, at m=2 or the line width is half of the pitch, all the even order scattering peaks vanish; at m=3 the intensity of the $3^{rd}$ order, the $6^{th}$ order and the $9^{th}$ order vanishes.

Figure 4A:
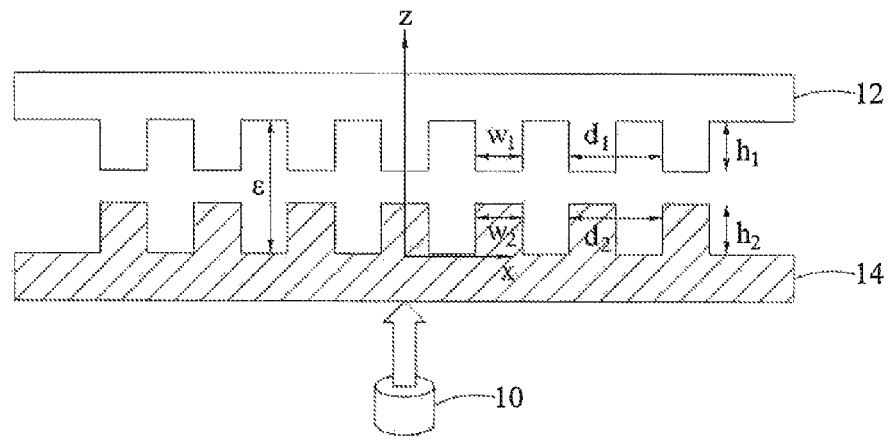
FIG. 4a is a schematic diagram illustrating the tSAXS measurement including a target object and an enhancement grating object when $h_2=h_1$, $d_2=d_1$ and $w_2=w_1$ in perfect alignment according to the disclosure.

Also, Eq. (3) depicts a perfect alignment between the enhancement grating object 14 and the target object 12 as illustrated in FIG. 4a. In view of a misalignment or a lateral shift by $\eta$, Eq. (3) is changed to:

$$I(q_x) = \Delta b_1^2 \times F_1^2(q_x) + \Delta b_2^2 \times F_2^2(q_x) + 2\Delta b_1 \Delta b_2 \cos(q_x \eta) |F_1(q_x) F_2(q_x)| \quad (3')$$

The value of $\eta$, by definition, has to be less than or equal to $d_1/2$, where $d_1$ denotes the pitch of the target object 12.

Preferably, the value of $\Delta b_2$ is greater than that of $\Delta b_1$ by choosing a high electron density material and a tall line height; i.e., with both $\rho_1 > \rho_2$ and $h_2 > h_1$ whenever it is possible. Moreover, $\Delta b_i$ is proportional to the product of $\rho_i$ and $h_i$. The ratio of $$\frac{\Delta b_2}{\Delta b_1} = f$$

is further defined, Eq. (3') can be written as:

$$I(q_x)/\Delta b_1^2 = 2f \cos(q_x \eta) F_1(q_x) F_2(q_x) + F_1^2(q_x) + \eta^2 F_2^2(q_x) \quad (3'')$$

The first term of Eq. (3'') represents amplification of the observed scattering intensity by the interaction between the target object 12 and the enhancement grating object 14. It is important to properly control the value of $\eta$, such that the magnitude of $2 \cos(q_x \eta) F_1(q_x) F_2(q_x)$ is much greater than $F_1^2(q_x)$ alone, whereas and the sign of the former term is often immaterial.

In order to realize certain amplification, the pitch of the enhancement grating object, $d_2$ has to follow the condition as $d_2=\alpha \times d_1$, where $\alpha$ may be ... 1/4, 1/3, 1/2, 1, 2, 3, 4, ... etc. Explicitly the conditions for certain amplification to be realized at a given $q_x$ are: (a) overlap of certain peak positions of two objects, or $$n_1 \frac{2\pi}{d_1} = n_2 \frac{2\pi}{d_2},$$

and (b) the quantity $$n_i \frac{w_i}{d_i}$$

inside the parenthesis of Eq. (4) for the target object 12 is NOT an integer; otherwise, the intensity of the $n_{th}$ peak becomes nil.

Since $d_2$ can be expressed as $\alpha \times d_1$, the condition (a) becomes $n_2=\alpha \times n_1$. At $\alpha=1$, all the peak positions between these two grating objects overlap. When $\alpha=2$, the $2^{nd}$ peak of the enhancement grating object 14 coincides with the first peak of the target object 12, the $4^{th}$ peak of the enhancement grating object 14 coincides with the $2^{nd}$ peak of the target object 12 and so on. Before amplification of the peak intensity of the target object 12 can be realized, the condition (b) indicates that the ratio $$\frac{w}{d}$$

cannot be $$\frac{1}{2}$$

with $\alpha=2$; otherwise, all the even order peaks will vanish. At the ratio equal to 1/4, the $4^{th}$, $8^{th}$, $12^{th}$, ... orders will disappear.

When $\alpha=1/2$, 1/3, 1/4, ..., the first order peak of the target object 12 is no longer to be amplified, the $2^{nd}$, $3^{rd}$ and $4^{th}$ orders will get amplified by the first peak of the enhancement object 14 respectively as long as the condition (b) is fulfilled.

For a pair of $n_1^{th}$ and $n_2^{th}$ peaks coexisted at a given $q_x$, the interaction or the amplification term of Eq. (3") can be expressed as:

$$2f\cos(q_x\eta)F_1(q_x)F_2(q_x) = 8f \frac{\cos(q_x\eta)}{n_1 \times n_2} \sin\left(n_1\pi\frac{w_1}{d_1}\right)\sin\left(n_2\pi\frac{w_2}{d_2}\right) \quad (5)$$

The denominator $n_1 \times n_2$ of Eq. (5) indicates that the extent of amplification is more pronounced when the low order peaks are invoked.

The disclosure will be more specifically described by the followings embodiments. However, these embodiments are not intended to limit the scope of the disclosure.

EMBODIMENTS

Embodiment 1:

In embodiment 1 of the disclosure, both the target object 12 and enhancement grating object 14 are identical in material and $h_2=h_1$, hence $f=1$. Moreover, $d_2=d_1$, hence $\alpha=1$. The line width is half of the pitch for both the enhancement grating object 14 and the target object 12, i.e., $m_1=m_2=2$.

Figure 4B:
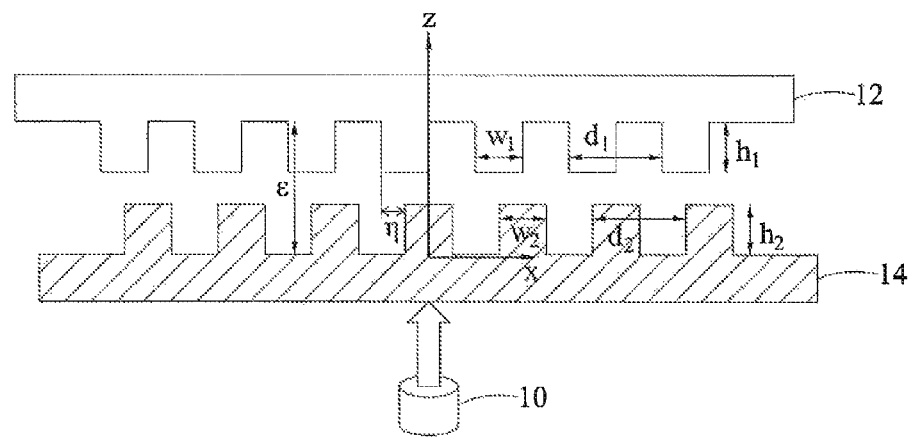
FIG. 4b is a schematic diagram illustrating a target object and an enhancement grating object when $h_2=h_1$, $d_2=d_1$ and $w_2=w_1$ with a lateral shift $\eta$ in the relative position between these two objects according to the disclosure.

As shown in FIG. 4b and FIG. 5, both the target object 12 and the enhancement grating object 14 can be aligned with a shift $\eta$ in the x-direction. The magnitudes of three terms of Eq. (3") are as follows:

$$F_1^2(q_x) \quad (6a)$$

$$F_2^2(q_x)=F_1^2(q_x) \quad (6b)$$

$$2\cos(q_x\eta)F_1(q_x)F_2(q_x)=2\cos(q_x\eta)F_1^2(q_x) \quad (6c)$$

All the peak positions are identical at $$q_x = n_1\frac{2\pi}{d_1} = n_2\frac{2\pi}{d_2}.$$

According to embodiment 1 of the disclosure, Eq. (3") becomes:

$$I(q_x) \propto 2F_1^2(q_x)+2\cos(q_x\eta)F_1^2(q_x) \quad (7)$$

It should be noticed that the value of $\cos(q_x\eta)$ plays an important role in Eq. (7). Considering $\cos(q_x\eta)$ at $$q_x = \frac{2\pi n_1}{d_1},$$

five special cases may be considered as follows:

(I) $\cos(q_x\eta)=1$

In case (I), $q_x\eta=0$ is required; that is, $\eta=0$ or $\eta \to 0$. The alignment of the target object 12 with the enhancement grating object 14 is perfect, as shown in FIG. 5a. For all the peak positions, the following equation can be obtained.

$$I \propto 2F_1^2(q_x)+2\cos(q_x\eta)F_1^2(q_x)=4F_1^2(q_x)$$

(II) $\cos(q_x\eta)=0$

In case (II), $q_x\eta=\pi/2$ is required; that is, $$\eta \times \left(\frac{2\pi n}{d_1}\right) = \frac{n\pi}{2},$$

where n is an odd number integer and the above condition leads to $$\eta = \frac{d_1}{4},$$

as shown in FIG. 5b. Thus, for all the peak positions, the following equation can be obtained.

$$I \propto 2F_1^2(q_x)+2\cos(q_x\eta)F_1^2(q)=2F_1^2(q_x)$$

For all the even order peaks, the intensity remains as $4F_1^2(q_x)$.

(III) $\cos(q_x\eta)=-1$

In case (III), $q_x\eta=\pi$ is required; that is $$\eta \times \left(\frac{2\pi n}{d_1}\right) = n\pi,$$

where n is an odd number integer and the above condition leads to $$\eta = \frac{d_1}{2},$$

as shown in FIG. 5c. For all the peak positions, the following equation can be obtained.

$$I \propto 2F_1^2(q_x) + 2\cos(q_x\eta)F_1^2(q_x) = 0$$

For all the even order peaks, the intensity recovers to $4F_1^2(q_x)$.

$$\cos(q_x\eta) = \frac{1}{2} \tag{IV}$$

In case (IV), $$q_x\eta = \frac{\pi}{3} \text{ or } q_x\eta = \frac{5\pi}{3}$$

is required; that is, $$\eta \times \left(\frac{2\pi n}{d_1}\right) = \frac{n\pi}{3}$$

this condition leads to $$\eta = \frac{d_1}{6}, \text{ and } \eta \times \left(\frac{2\pi n}{d_1}\right) = \frac{5n\pi}{3}$$

this condition leads to $$\eta = \frac{5d_1}{6}.$$

For all peak numbers n=1, 5, 7, 11, 13, . . . , the scattering intensity is as follows:

$$I \propto 2F_1^2(q_x) + F_1^2(q_x) = 3F_1^2(q_x)$$

For all the peak numbers n=2, 4, 8, 10, . . . , the scattering intensity is as follows:

$$I \propto 2F_1^2(q_x) - F_1^2(q_x) = F_1^2(q_x)$$

For all the peak numbers n=3, 9, . . . , the scattering intensity is as follows:

$$I \propto 2F_1^2(q_x) - 2F_1^2(q_x) = 0$$

For all the peak numbers n=6, 12, . . . , the scattering intensity is as follows:

$$I \propto 2F_1^2(q_x) + 2F_1^2(q_x) = 4F_1^2(q_x) \tag{V}$$

$$\cos(q_x\eta) = -\frac{1}{2}$$

In case (V), $$q_x\eta = \frac{2\pi}{3}$$

or $$q_x\eta = \frac{4\pi}{3}$$

is required; that is, $$\eta \times \left(\frac{2\pi n}{d_1}\right) = \frac{2n\pi}{3}$$

and this leads to $$\eta = \frac{d_1}{3},$$

$$\eta \times \left(\frac{2\pi n}{d_1}\right) = \frac{4n\pi}{3}$$

and this leads to $$\eta = \frac{2d_1}{3}.$$

For all the peak number n=1, 2, 4, 5, 7, . . . , the scattering intensity is as follows:

$$I \propto 2F_1^2(q_x) - F_1^2(q_x) = F_1^2(q_x)$$

For all the peak number n=3, 6, 9, . . . , the scattering intensity is as follows:

$$I \propto 2F_1^2(q_x) + 2F_1^2(q_x) = 4F_1^2(q_x)$$

According to the disclosure, Table 1 summarizes the peak intensities under cases (I)-(V) and others.

The aforesaid five cases demonstrate that the details of the amplification depend on the alignment of the enhancement grating object 14 with respect to the target object 12. The type of sensitivity provides a possible experimental route to quantify the extent of amplification when the value of $\eta$ is swiped with a step less than a fraction of $d_1$. The intensity enhancement of the target object 12 depends on the alignment in the x-direction. Once in the perfect alignment, the peak intensity can be up to 4 times for all the peaks. When the alignment starts to shift from 0 to $$\frac{d_1}{4}$$

(half of the line width), the intensity drops to 2 times for all the odd number peaks. When the alignment shifts from $$\frac{d_1}{4} \text{ to } \frac{d_1}{3}$$

(two third of the line width), no enhancement is found at the $1^{st}, 2^{nd}, 4^{th}, 5^{th}, \ldots$ peaks. When the alignment shifts from $$\frac{d_1}{3} \text{ to } \frac{d_1}{2}$$

(line width), no scattering can be observed for all the odd number peaks.

Embodiment 2:

The conditions of embodiment 2 are the same with those of embodiment 1. However, the target object 12 is made of Si, and the enhancement grating object is made of Cu, as shown in FIG. 6.

TABLE 1

Intensities of each peak under cases (I)-(V) and others

| | | $n_i$, the order of scattering peak | | | | | | | | | |
|---|---|---|---|---|---|---|---|---|---|---|---|
| qη | η | 1 | 2 | 3 | 4 | 5 | 6 | 7 | 8 | 9 | 10 |
| 0 | 0 | $4F_1^2$ | $4F_1^2$ | $4F_1^2$ | $4F_1^2$ | $4F_1^2$ | $4F_1^2$ | $4F_1^2$ | $4F_1^2$ | $4F_1^2$ | $4F_1^2$ |
| $\frac{\pi}{3}$ | $\frac{d_1}{6}$ | $3F_1^2$ | $1F_1^2$ | 0 | $1F_1^2$ | $3F_1^2$ | $4F_1^2$ | $3F_1^2$ | $1F_1^2$ | 0 | $1F_1^2$ |
| $\frac{\pi}{2}$ | $\frac{d_1}{4}$ | $2F_1^2$ | $4F_1^2$ | $2F_1^2$ | $4F_1^2$ | $2F_1^2$ | $4F_1^2$ | $2F_1^2$ | $4F_1^2$ | $2F_1^2$ | $4F_1^2$ |
| $\frac{2\pi}{3}$ | $\frac{d_1}{3}$ | $1F_1^2$ | $1F_1^2$ | $4F_1^2$ | $1F_1^2$ | $1F_1^2$ | $4F_1^2$ | $1F_1^2$ | $1F_1^2$ | $4F_1^2$ | $1F_1^2$ |
| $\pi$ | $\frac{d_1}{2}$ | 0 | $4F_1^2$ | 0 | $4F_1^2$ | 0 | $4F_1^2$ | 0 | $4F_1^2$ | 0 | $4F_1^2$ |
| $\frac{4\pi}{3}$ | $\frac{2d_1}{3}$ | $1F_1^2$ | $1F_1^2$ | $4F_1^2$ | $1F_1^2$ | $1F_1^2$ | $4F_1^2$ | $1F_1^2$ | $1F_1^2$ | $4F_1^2$ | $1F_1^2$ |
| $\frac{3\pi}{2}$ | $\frac{3d_1}{4}$ | $2F_1^2$ | $4F_1^2$ | $2F_1^2$ | $4F_1^2$ | $2F_1^2$ | $4F_1^2$ | $2F_1^2$ | $4F_1^2$ | $2F_1^2$ | $4F_1^2$ |
| $\frac{5\pi}{3}$ | $\frac{5d_1}{6}$ | $3F_1^2$ | $1F_1^2$ | 0 | $1F_1^2$ | $3F_1^2$ | $4F_1^2$ | $3F_1^2$ | $1F_1^2$ | 0 | $1F_1^2$ |
| $2\pi$ | 0 | $4F_1^2$ | $4F_1^2$ | $4F_1^2$ | $4F_1^2$ | $4F_1^2$ | $4F_1^2$ | $4F_1^2$ | $4F_1^2$ | $4F_1^2$ | $4F_1^2$ |

Since the enhancement grating object is made of Cu and the target object 12 is made of Si, the electron intensity of the enhancement grating object is $f \sim 3.42$ times that of the target object 12.

According to embodiment 2 of the disclosure, the magnitudes of three terms of Eq. (3") are as follows:

$$F_1^2(q_x) \quad (8a)$$

$$F_2^2(q_x) \sim f^2 F_1^2(q_x) = 11.70 F_1^2(q_x) \quad (8b)$$

$$2\cos(q_x\eta)F_1(q_x)F_2(q_x) = (2f)\cos(q_x\eta)F_1^2(q_x) = 6.84 \cos(q_x\eta)F_1^2(q_x) \quad (8c)$$

Therefore, the Eq. (3") becomes:

$$I(q_x) \propto 12.70 F_1^2(q_x) + 6.84 \cos(q_x\delta)F_1^2(q_x) \quad (9)$$

The value of $\cos(q_x\eta)$ ranges from $-1$ to $+1$. Thus, the intensity ranges from $+5.86F_1^2(q_x)$ to $+19.54F_1^2(q_x)$. The intensity enhancement factor due to the interaction of the enhancement object with the target object can reach 6.84 under the condition of a perfect alignment.

Embodiment 3:

The conditions of embodiment 3 are the same with those of embodiment 1, but the feature height of the enhancement grating object is selected to be $h_2=10h_1$, i.e. $f=10$ and let the two objects having identical electron density, as shown in FIG. 7, the magnitudes of three terms of Eq. (3") are as follows:

$$F_1^2(q_x) \quad (10a)$$

$$F_2^2(q_x) = f^2 F_1^2(q_x) = 100 F_1^2(q_x) \quad (10b)$$

$$2\cos(q_x\eta)F_1(q_x)F_2(q_x) \sim (2f)\cos(q_x\eta)F_1^2(q_x) = 20 \cos(q_x\eta)F_1^2(q_x) \quad (10c)$$

All the positions q are located at $$\frac{2n_1\pi}{d_1} \text{ or } \frac{2n_2\pi}{d_2}.$$

Therefore, the Eq. (3") becomes:

$$I(q_x) \propto 101 F_1^2(q_x) + 20 \cos(q_x\eta)F_1^2(q_x) \quad (11)$$

Since the value of $\cos(q_x\eta)$ ranges from $-1$ to $+1$. Thus, the intensity ranges from $+81F_1^2(q_x)$ to $+121F_1^2(q_x)$ and a maximum intensity enhancement factor of 20. By collecting tSAXS data at different values of η, a change in observed intensities can be as large as $40F_1^2(q_x)$ Embodiment 4:

The conditions of embodiment 4 are the same with those of embodiment 1. The line width to pitch ratio is identical for these two objects, i.e.

$$\frac{w_1}{d_1} = \frac{w_2}{d_2} = \frac{1}{m}.$$

The pitch of the enhancement grating object is $d_2 = 3d_1$, as shown in FIG. 8. Since both the target object 12 and the enhancement grating object 14 are identical in material and in grating height, i.e., $f=1$. The scattering intensity overlaps at $n_2 = 3n_1$, i.e., the $3^{rd}$ peak of the enhancement grating object interacts with the $1^{st}$ peak of the target object 12 and so on.

According to embodiment 4 of the disclosure, the magnitudes of three terms of Eq. (3") are as follows:

$$F_1^2(q_x) \quad (12a)$$

$$F_2^2(q_x) \sim \frac{4}{(3n_1)^2}\left(\sin\frac{3n_1\pi}{m}\right)^2 = \left(\frac{1}{9}\right)\frac{\left(\sin\frac{3n_1\pi}{m}\right)^2}{\left(\sin\frac{n_1\pi}{m}\right)^2}F_1^2(q_x) \quad (12b)$$

$$2f\cos(q_x\eta)F_1(q_x)F_2(q_x) \sim \frac{8}{3n_1^2}\cos(q_x\eta)\sin\left(\frac{3n_1\pi}{m}\right)\sin\left(\frac{n_1\pi}{m}\right) = \quad (12c)$$

$$\frac{2}{3}\cos(q\eta)\frac{\sin\left(\frac{3n_1\pi}{m}\right)}{\sin\left(\frac{n_1\pi}{m}\right)}F_1^2(q)$$

In Eqs. (12a)-(12c), $$q_x = \frac{2n_1\pi}{d_1} = \frac{2n_2\pi}{d_2}.$$

It is noteworthy that the value of m plays an important role. For example, in the case of $d_2 = 3d_1$, the condition of $m=3$ leads to the vanishing of both the $2^{nd}$ term and the $3^{rd}$ term given as Eq. (12b) and Eq. (12c), respectively; no amplification effect can be observed at any peak position of the target object 12.

According to the disclosure, embodiments 1-4 amply demonstrate that the product of the grating height and the electron density (i.e., the factor $f$), the alignment between the target object 12 and the enhancement grating object 14, the pitch and its ratio to line width affect the extent of intensity amplification of the target object 12.

Embodiment 5:

In embodiment 5 of the disclosure, the target object 12 is made of Si, but the enhancement grating object 14 is made of Cu. Let $h_2 = 10h_1$ and $d_2 = 3d_1$, the line width is half of the pitch for both the enhancement grating object 14 and the target object 12, i.e. $m_1 = m_2 = 2$. The pattern part of the enhancement grating object 14 is made of materials with a high electron density such as copper, silver, gold and others.

In this embodiment, given $f=34.2$, the positions $q_x$ are located at $$q_x = \frac{2n_1\pi}{d_1} = \frac{6n_1\pi}{d2}$$

or $n_2 = 3n_1$; i.e. the $3^{rd}$ peak from the enhancement grating object overlaps the first one of the target object and so on.

As such, according to embodiment 5 of the disclosure, the magnitudes of three terms of Eq. (3") are as follows:

$$F_1^2(q_x) \quad (12a)$$

$$F_2^2(q_x) \sim \left(\frac{34.2^2}{3^2}\right)\frac{\sin\left(\frac{3n_1\pi}{2}\right)^2}{\sin\left(\frac{n_1\pi}{2}\right)^2}F_1^2(q_x) \cong 130F_1^2(q_x) \quad (12b)$$

$$2f\cos(q_x\eta)F_1(q_x)F_2(q_x) \sim \left(\frac{2\times 34.2}{3}\right)\cos(q_x\eta)\frac{\sin\left(\frac{3n_1\pi}{2}\right)}{\sin\left(\frac{n_1\pi}{2}\right)}F_1^2(q_x) \cong \quad (12c)$$

$$-23\cos(q_x\eta)F_1^2(q)$$

for all the odd numbers $n_1$, and nil for the rest.

As in previous cases the value of $\cos(q_x\eta)$ plays an important role in Eqs. (13a)-(13c). Considering the $3^{rd}$ terms, it has a range between $+23F_1^2(q_x)$ and $-23F_1^2(q_x)$.

At $\eta \to 0$ (i.e., zero misalignment between two objects), the scattering intensities at all the odd number peaks decrease by $23F_1^2(q_x)$. As $$\eta \to \frac{d_1}{2}$$

the value of $\cos(q_x\eta)$ approaches $-1$ for all the intensities of all the odd number peaks and the value of $\cos(q_x\eta)$ approaches $-1$ for the $3^{rd}$ and the $9^{th}$ peak positions as $$\eta \to \frac{d_1}{6}$$

while $\cos(q_x\eta)$ approaches 0.5 for $n_1=1$, 3 and etc. With a precise control of $\eta$, a predictable change in intensity of the odd number peaks from the target object 12 with a magnitude between $\pm 23F_1^2(q_x)$ can be observed. Accordingly, the results will facilitate the detection of $2\cos(q_x\eta)F_1(q_x)F_2(q_x)$ by scanning $\eta$ between $$\pm \frac{d_1}{2}.$$

According to the disclosure, the pattern part of the enhancement grating object 14 is "facing" the pattern part of the target object 12 for the purpose of ensuring these two patterned parts within the coherence length of the probing X-ray (or light) beams. This configuration minimizes the distance between the target object 12 and the enhancement grating object 14.

Embodiment 6:

In this embodiment, the target object 12 is made of Si, and the enhancement grating object 14 is made of Cu. The heights of these two objects are the same; that is, $h_2 = h_1$ hence we have $f=3.42$. The pitch of the enhancement grating object is $$d_2 = \frac{1}{2}d_1.$$

The line width is one third of the pitch for both the enhancement grating object 14 and the target object 12; that is, $m_1=m_2=3$, as shown in FIG. 10.

The $2^{nd}$, $4^{th}$, $6^{th}$ ... peaks of the target object 12 overlap with the $1^{st}$, $2^{nd}$, $3^{rd}$, ... peaks of the enhancement grating object 14. In other words, the condition $n_1=2n_2$ indicates that $n_1$ has to be an even number. The condition m=2 will lead to all the even number peaks to vanish, hence it is avoided in this embodiment. As such the magnitudes of three terms of Eq. (3") are as follows:

$$F_1^2(q_x) \tag{14a}$$

$$F_2^2(q_x) \sim (3.42^2 \times 2^2)\frac{\sin\left(\frac{n_1\pi}{6}\right)^2}{\sin\left(\frac{n_1\pi}{3}\right)^2}F_1^2(q_x) \cong 47 F_1^2(q_x) \tag{14b}$$

The term $$\frac{\sin\left(\frac{n_1\pi}{6}\right)^2}{\sin\left(\frac{n_1\pi}{3}\right)^2}$$

in Eq. (14b) equals to unity for all the even number $n_1$.

$$2f\cos(q_x\eta)F_1(q_x)F_2(q_x) \sim 2f\cos(q_x\eta)\frac{n_1}{n_2}\frac{\sin\left(\frac{n_2\pi}{m}\right)}{\sin\left(\frac{n_1\pi}{m}\right)}F_1^2(q_x) = \tag{14c}$$

$$(2\times 3.42 \times 2)\cos(q_x\eta)\frac{\sin\left(\frac{n_1\pi}{6}\right)}{\sin\left(\frac{n_1\pi}{3}\right)}F_1^2(q_x) = 14\cos(q_x\eta)s(n_1)F_1^2(q_x)$$

where $$q_x = \frac{2n_1\pi}{d_1}$$

for $n_1=2, 4, 6, \ldots$ and the term $s(n_1)$, standing for $$\frac{\sin\left(\frac{n_1\pi}{6}\right)}{\sin\left(\frac{n_1\pi}{3}\right)},$$

is 1, −1 and −0.5 ... as $n_1=2, 4, 6$ ... Therefore, based on the above conditions, Eq. (3") becomes $$I(q_x) \propto 48F_1^2(q_x)+14\cos(q_x\eta)s(n_1)F_1^2(q_x) \tag{15}$$

Moreover, it is important to note that the intensity enhancement for the target object 12 takes place at its $2^{nd}$, $4^{th}$, $6^{th}$ peaks. Even with an enhancement factor of 14, the observed intensity at the $2^{nd}$ peak is not going to be much higher than that of the first peak over which there is no amplification. In general, the intensity of the first peak is much greater than the rest and it is desirable to design an enhancement object capable to amplify the intensity of the first peak from the target object.

Embodiment 7:

The intensity enhancement may be further increased if the pitch height of the enhancement grating object 14 is larger than that of the target object 12. For example, $h_2=5h_1$ and $f=17.1$, as shown in FIG. 11 where the target object 12 is made of Si, and the enhancement grating object is made of Cu. With all the other feature dimensions identical to those of embodiment 6, the magnitudes of three terms of Eq. (3") are as follows:

$$F_1^2(q_x) \tag{16a}$$

$$F_2^2(q) \sim (3.42\times 5\times 2)^2 F_1^2(q_x)=1170F_1^2(q_x) \tag{16b}$$

$$2\cos(q_x\eta)F_1(q_x)F_2(q_x)=(2\times 5\times 3.42\times 2)\cos(q_x\eta)s(n_1) \\ F_1^2(q_x)=68.4\cos(q_x\eta)s(n_1)F_1^2(q_x) \tag{16c}$$

Thus, Eq. (4) becomes, $$I(q) \propto 1170F_1^2(q_x)+68.4\cos(q_x\eta)s(n_1)F_1^2(q_x) \tag{17}$$

The enhancement ranges from $-68.4F_1^2(q_x)$ to $+68.4F_1^2(q_x)$.

According to the disclosure, embodiments 1-7 are only used to exemplify the apparatus for enhancing scattering intensity using the tSAXS technique, and should not be construed as to limit the disclosure. As such, the above embodiments of the disclosure can be modified and altered by those with ordinary skill in the art, without departing from the spirit and scope of the disclosure as defined in the following appended claims.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching. The embodiments were chosen and described in order to explain the principles of the disclosure, i.e. placing an object within the longitudinal coherence length of the target object to enhance the scattering signal from the target object, and their practical application so as to activate others skilled in the art to utilize the invention and various embodiments and with various modifications as are suited to the particular use contemplated.

Therefore, the disclosure provides an apparatus for amplifying scattering intensities from a target object during X-ray scattering measurements. The measurement speed and signal quality are improved due to amplification of X-ray scattering. The analyses of critical dimension evaluations, shapes and variations in pitches can be facilitated when HVM is performed.

Accordingly, solutions to the problems described above have been long sought, but prior developments have not taught or suggested any solutions and, thus, solutions to the problems have long eluded those skilled in the art. Therefore, there is a heretofore-unaddressed need to overcome deficiencies and shortcomings described above.

The resulting apparatus for enhancement scattering intensity of the disclosure is cost-effective, uncomplicated, highly versatile and effective, and can be implemented by adopting known semiconductor technology for efficient and economical manufacturing, application and utilization. It valuably supports and services the trend of reducing costs, simplifying systems, and increasing performance.

While the disclosure has been described in conjunction with a specific best mode, it is to be understood that many alternatives, modifications, and variations will be apparent to those skilled in the art in light of the aforesaid description.

Accordingly, it is intended to embrace all such alternatives, modifications, and variations that fall within the scope of the included claims. All matters heretofore set forth herein or shown in the accompanying drawings are to be interpreted in an illustrative and non-limiting sense.

What is claimed is:

1. An apparatus for amplifying scattering intensity during transmission small-angle X-ray scattering (tSAXS) measurements, comprising:
    an enhancement grating object positioned within a longitudinal coherence length of an incident X-ray from a target object, wherein the enhancement grating object is configured to enhance X-ray scattering intensity from the target object; and
    a placement mechanism configured to place the enhancement grating object with nanometer precision with respect to the target object in both a lateral and a longitudinal directions.

2. The apparatus according to claim 1, wherein the enhancement grating object is positioned either at a front of the target object or at a back of the target object.

3. The apparatus according to claim 1, wherein a pattern part of the enhancement grating object faces a pattern part of the target object.

4. The apparatus according to claim 1, wherein the enhancement grating object is made of a material the same as or different from the target object.

5. The apparatus according to claim 1, wherein a height of a pattern part of the enhancement grating object is larger than a height of a pattern part of the target object by a factor greater than unity.

6. The apparatus according to claim 1, wherein a pitch of a pattern part of the enhancement grating object is $\alpha$ times larger than a pitch of a pattern part of the target object, or $1/\alpha$ of a height of the pattern part of the target object, where $\alpha$ is an integer greater than or equal to unity.

7. The apparatus according to claim 1, wherein a pattern part of the enhancement grating object is made of materials with a high electron density selected from a group consisting of copper, silver, gold and others.

8. The apparatus according to claim 1, wherein the enhancement grating object is configured to be shifted laterally with respect to the target object with nanometer precision during tSAXS measurements.

9. The apparatus according to claim 1, wherein the enhancement grating object is configured to be shifted longitudinally with respect to the target object with nanometer precision during tSAXS measurements.

10. The apparatus according to claim 1, wherein the enhancement grating object is used as a reference object, the target object has a single or multiple layered structure, and the enhancement grating object is configured to facilitate critical dimension (CD) characterization of the target object with the single or multiple layered structure.

11. The apparatus according to claim 1, wherein a source of the incident X-ray source is selected from a group consisting a laboratory source, a synchrotron light source providing a high X-ray flux and other X-ray sources.

12. The apparatus according to claim 1, wherein the enhancement grating object is selected from a group consisting of a one-dimensional (1-D) grating object, a two-dimensional (2-D) grating object, arrays of holes, pillars and other periodical structures.

\* \* \* \* \*